United States Patent [19]
Naujokas

[11] Patent Number: 5,952,520
[45] Date of Patent: Sep. 14, 1999

[54] RECOVERY OF ESTER MONOMER FROM POLYESTER RESINS

[75] Inventor: Andrius Algimantas Naujokas, Webster, N.Y.

[73] Assignee: Eastman Kodak Company, Rochester, N.Y.

[21] Appl. No.: 08/678,006

[22] Filed: Jul. 10, 1996

[51] Int. Cl.[6] .................................................. C07C 67/60
[52] U.S. Cl. .............................................. 560/78; 560/96
[58] Field of Search ........................................ 560/78, 96

[56] References Cited

U.S. PATENT DOCUMENTS

| | | | |
|---|---|---|---|
| 3,949,007 | 4/1976 | Grolig et al. ............................ | 260/635 |
| 4,163,860 | 8/1979 | Delattre et al. ........................... | 560/96 |
| 5,051,528 | 9/1991 | Naujokas et al. ......................... | 560/78 |
| 5,298,530 | 3/1994 | Gamble et al. ......................... | 521/48.5 |
| 5,393,916 | 2/1995 | Gamble et al. ............................ | 560/78 |
| 5,414,022 | 5/1995 | Toot, Jr. et al. ........................... | 521/48 |

FOREIGN PATENT DOCUMENTS 1081681  12/1954  France ......................................... 14/1

*Primary Examiner*—Samuel Barts
*Attorney, Agent, or Firm*—Arthur H. Rosenstein

[57] ABSTRACT

There is described a process for improving the yield of diester monomer recovered from the depolymerization of polyethylene terephthalate by converting a mixture of dimethyl terephthalate and methylhydroxyethyl terephthalate to predominantly dimethyl terephthalate by treating that mixture with a mixture of an alcohol and an alkali metal hydroxide at a temperature up to the boiling point of the alcohol.

7 Claims, 1 Drawing Sheet

RECOVERY OF ESTER MONOMER FROM POLYESTER RESINS

FIELD OF INVENTION

This invention relates to improving the yield of difunctional ester in a process of recovering monomer components from condensation-type polyester resins such as polyethylene terephthalate.

BACKGROUND OF THE INVENTION

Polyester resins have found widespread use in varied applications. Polyester resins, such as polyethylene terephthalate, are used in films, including photographic film, in fibers, and in food and beverage containers. Various methods have been disclosed for the depolymerization of such resins into their component monomers, such as ethylene glycol and terephthalic acid, or derivatives thereof, so that they could be reused.

Some of these methods are described in such patents as U.S. Pat. Nos. 3,037,050, 3,321,510, 3,884,850, 3,907,868, 4,163,860, 4,578,502, 4,620,032, 4,876,378 and 5,095,145, and in European Published Patent Application 0 484 963 published May 13, 1992.

A particularly useful technique for recovering scrap polyester is described in a series of patent that begins with Naujokas et al. U.S. Pat. No. 5,051,528. This patent describes a process of recovering ethylene glycol and dimethyl terephthalate from polyethylene terephthalate scrap resins by dissolving the polyester resin in oligomers of the same monomers as present in the polyester, passing superheated methanol through the solution and recovering ethylene glycol and dimethyl terephthalate.

Gamble et al. U.S. Pat. No. 5,298,530, issued Mar. 29, 1994 describes improvements in this process. In the improved process scrap resin is combined with melt from the reactor in a dissolver, and the dissolver melt is transferred to the reactor for contact with super-heated methanol. In the reactor, polymers and oligomers are further depolymerized into component glycol and ester monomers, which are then recovered.

Further improvements and variations of this process are described in Gamble et al. U.S. Pat. No. 5,393,916 issued Feb. 28, 1995 and in Toot et al. U.S. Pat. No. 5,414,022 issued May 9, 1995.

The processes described in these patents reverse the polymerization reaction by which the polyethylene terephthalate is formed by depolymerizing polyethylene terephthalate (PET) to dimethyl terephthalate (DMT) and ethylene glycol (EG). DMT and EG are recovered and reused. If the depolymerization reaction does not go to completion, an intermediate half ester, methylhydroxyethyl terephthalate (MHET), is present in the product stream. MHET is relatively soluble in methanol and will remain in solution when DMT is separated from other components in the product stream by crystallization, thus reducing the yield of DMT from that theoretically possible. Furthermore, when the liquid phase, containing methanol and EG, is separated from the DMT crystals, any MHET present will go with the methanol, where it will complicate the recovery of methanol and EG.

Thus, it would be desirable to have a process for converting MHET to DMT during the recovery of the latter, so as to increase the yield of DMT and to eliminate the need to separate MHET in subsequent recovery operations.

SUMMARY OF THE INVENTION

I have found that a mixture of an alcohol and an alkali metal hydroxide acts as a catalyst for the conversion of MHET to DMT. Thus, the present invention provides a process for converting a first mixture (1) of dimethyl terephthalate and methylhydroxyethyl terephthalate to predominantly (greater than 99 weight percent) dimethyl terephthalate by treating the mixture with a second mixture of an alcohol and an alkali metal hydroxide for a period of 0.5 to 5 minutes at a temperature in the range of from 0° C. to the boiling point of the alcohol, and at a pressure in the range of 0 to 30 psig.

Metal alkoxides are described in Grolig et al. U.S. Pat. No. 3,949,007 issued Apr. 6, 1976, Delattre et al U.S. Pat. No. 4,163,860 issued Aug. 7, 1979, and French Patent 1,081,681, published Dec. 22, 1954 (which is summarized in U.S. Pat. No. 4,163,860) for use as depolymerization or transesterification catalysts. However, the processes described in these patents are different from the present process and use the alkoxide at a different point for a different purpose.

The process of the present invention provides a simple, convenient way of purifying and increasing the yield of the diester obtained by the depolymerization of polyester resins.

DETAILED DESCRIPTION OF THE INVENTION

Figure 1:
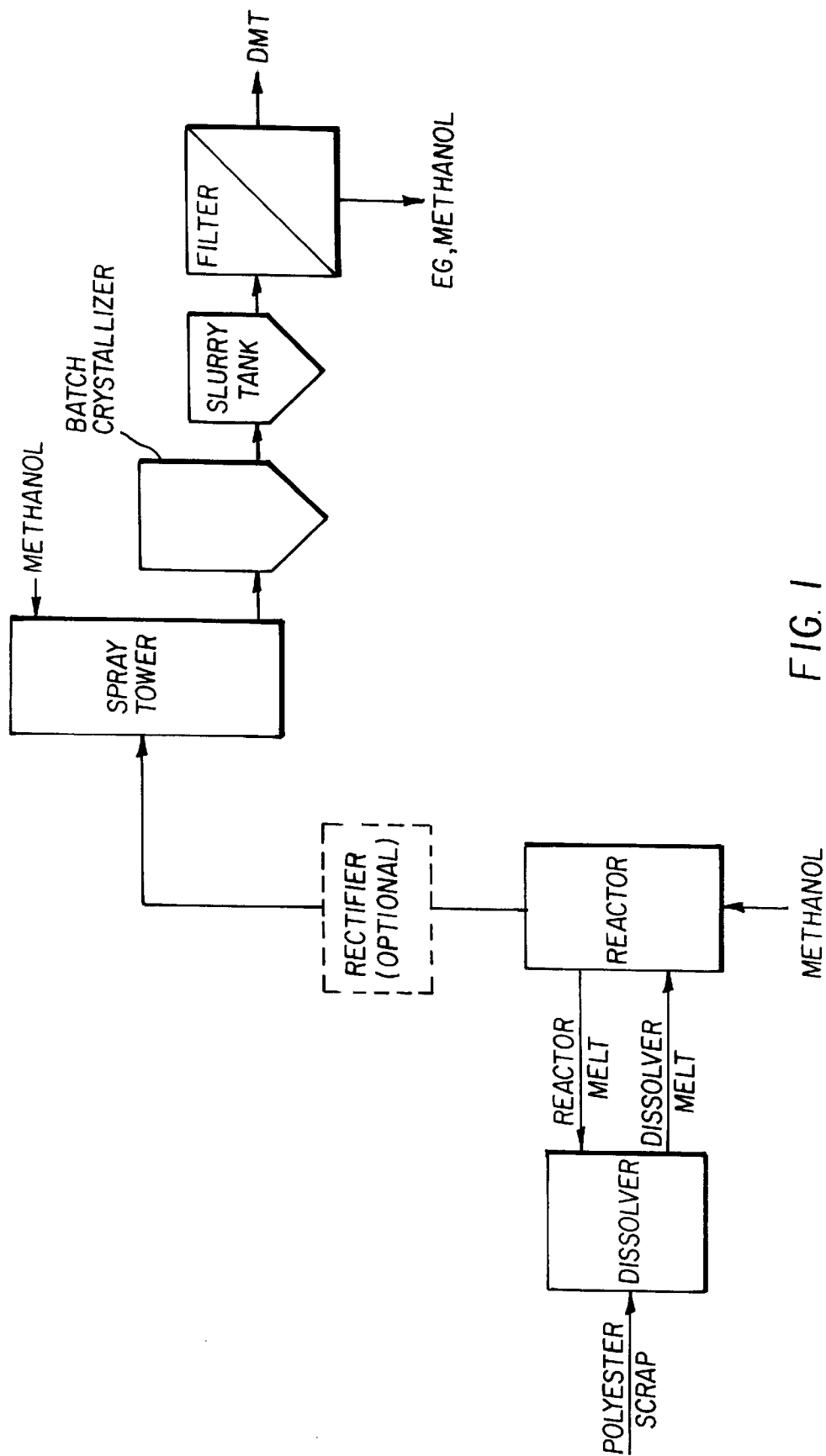
FIG. 1 is a schematic flow diagram illustrating apparatus in which the process of the present invention can be employed as part of a polyester scrap recovery process.

The present invention can be carried out as a batch process or a continuous process and applied to mixtures of DMT and MHET from whatever source obtained.

The mixture of DMT and MHET is contacted with a mixture of an alkali metal hydroxide in an alcohol. Preferred alkali metal hydroxides are sodium hydroxide and potassium hydroxide, although others can be used. If the ester desired is DMT, the alcohol should be methanol. If however, the process leads to a different ester, the corresponding alcohol is used, for example ethanol, propanol, butanol, hexanol, etc.

The proportions of alkali metal hydroxide to alcohol are not critical. There should be at least sufficient alcohol to react with the MHET to convert it to DMT. Typically, the mixture can comprise about 1 to 10 parts alkali metal hydroxide per 100 parts alcohol (by weight). The mixture of alkali metal hydroxide in alcohol is contacted with the DMT/MHET mixture to convert the MHET to DMT and EG. This can be accomplished at a temperature from about 0° C. to the boiling point of the alcohol used (64° C. for methanol at atmospheric pressure) and at a pressure from atmospheric pressure to slightly elevated pressure (0 psig to 30 psig.) Preferably the reaction is carried out at temperatures from about 15° C. to about 30° C.

The amount of the mixture of alkali metal hydroxide in alcohol contacted with the DMT/MHET mixture can vary over a wide range. Typically, from about 0.5 to 2.0 part by weight of the mixture of alkali metal hydroxide in alcohol is used per part by weight of the DMT/MHET mixture. The time of contact will vary depending upon the amount of MHET present in the mixture. Contact times of from several seconds to several minutes provide useful results.

The process of this invention can be performed as a batch process using DMT/MHET mixtures from whatever source derived. In a typical embodiment, mixture of DMT, MHET, EG and MeOH are formed during the depolymerization of PET. If the monomers are to be recovered for reuse, the components of the mixture must be separated and purified. A typical separation technique involves chilling the mixture in a spray tower, crystallizing the remaining DMT in a crystallizer to leave a slurry comprised of EG, DMT, MHET and MeOH, and then separating the solid phase containing DMT crystals from the liquid phase containing EG and MeOH. Any one of the spray tower, the crystallizer or the slurry storage are suitable locations to introduce the alcohol/alkali metal hydroxide mixture to effect conversion of MHET to DMT.

Thus, in one embodiment, the alcohol/alkali metal hydroxide mixture can prepared in a separate vessel and introduced into the crystallizer toward the end of the crystallization cycle. In another embodiment, the alcohol/alkali metal hydroxide mixture can be introduced into a slurry holding tank where the slurry is held prior to filtration. In yet another embodiment, the alcohol/alkali metal hydroxide mixture can be added to slurry as it is transported to a slurry holding tank.

In a preferred embodiment, the present invention is applied to mixtures of DMT and MHET obtained from low pressure methanolysis apparatus as described in U.S. Pat. No. 5,051,528.

The apparatus of FIG. 1. comprises:

a dissolver for receiving polyester, a reactor for depolymerizing polyester into monomer components, and recovery apparatus for separating monomer components and converting MHET to DMT.

In particular, the recovery apparatus can comprise:

a spray tower for cooling the monomer mixture and removing methanol from the recovery stream, a batch crystallizer for crystallizing DMT, a slurry tank for holding the mixture of solid DMT and liquid EG and MeOH, and a filter for separating solid DMT from liquid EG and MeOH.

In a preferred embodiment, this apparatus is used in a process which comprises the steps of:

a) adding polyester to the dissolver and combining it with melt from the reactor to reduce the chain length of the polyester, b) transferring reduced chain length polyester from the dissolver to the reactor, c) passing super-heated methanol through the reactor to depolymerize polyester into its constituent monomers, d) recovering and separating monomer components from the output of the reactor, where separation of the diester monomer is performed using the process described above.

In particular, the alcohol/alkali metal hydroxide mixture can be contacted with MHET present in any one of the spray tower, the crystallizer or the slurry tank.

In the apparatus of FIG. 1 a dissolver, a reactor and recovery apparatus are connected by the pipes, pumps and valves to transfer the materials in accordance with the process of the invention. Optionally included in this apparatus are a scrubber for recovering gases from the dissolver, and a rectifier for separating monomer components and methanol vapor exiting the reactor from higher boiling components that are returned to the reactor.

In practice, polyethylene terephthalate in a suitable form and size is introduced into the dissolver by any suitable means where it is liquefied and reduced in chain length. The dissolver can be run at atmospheric pressure. Thus, simple solids handling devices such as rotary air locks can be employed to introduce the polyester resin. Suitable means for introducing the polyester include an air conveyor, a screw feeder, an extruder, and the like.

The dissolver is equipped with means for heating its contents to a temperature of up to about 305° C. In practice the dissolver is maintained at a temperature in the range of 240 to 260° C.

The reactor melt can be introduced into the dissolver via suitable piping. Reactor melt introduced into the dissolver react with the polyester to shorten the average chain length. This initiates the depolymerization reaction and decreases the viscosity of the dissolver contents. In addition, there can be added to the dissolver an ester exchange catalyst, such as zinc acetate. Such catalysts are known in the art to facilitate the depolymerization process.

The reactor melt and dissolver melt comprise methanol, low molecular weight polyesters, monomers, monohydric alcohol-ended oligomers, glycols, dimethylterephthalate and methylhydroxyethyl terephthalate. The major difference between these two melts is the average chain length of the polyester.

The viscosity of the dissolver melt preferably is maintained in the range of 0.002 to 0.1 Pa·s. This is sufficiently low to permit the use of inexpensive pumping and heating means, and permits the reactor to be operated at optimum pressures to provide good yields of monomer. The flow rates of material in and out of the dissolver can be adjusted to maintain the viscosity at the desired level.

The dissolver also can be equipped with means for removing contaminants that are introduced with the polyester. Most contaminants are removed from the melt in the dissolver before introduction of the dissolver melt to reactor. Inorganic contaminants such as metals or sand are removed by a filter. Polyolefins and other contaminants that float on top of the dissolver melt are drawn off.

The gases which evolve in the dissolver contain monomers that preferably are recovered together with the monomers exiting the reactor. This can be accomplished by passing the gases to a scrubber where they are treated with and absorbed by liquid methanol. This material can be passed to the recovery apparatus where it can be combined with material exiting the reactor.

Melt from the dissolver is transferred to the reactor by suitable piping and pumps. Super-heated methanol vapor can be provided to the reactor by conventional means. The methanol introduced into the reactor heats the reactor contents and acts as a depolymerization agent. The effectiveness of the super-heated methanol for heating the reactor contents and for stripping gases depends on its volumetric flow rate; the depolymerization rate in the reactor therefore is a function of the methanol flow rate to the reactor. Methanol is introduced into the reactor at a rate in the range of 2 to 6 parts by weight methanol per part polyester.

There exits the reactor a vapor stream comprising methanol, dimethyl terephthalate, glycols including ethylene glycol, diethylene glycol, and triethylene glycol, dimethyl isophthalate, cyclohexanedimethanol, and methylhydroxyethyl terephthalate. The vapor stream goes to recovery apparatus, where methanol can be recovered for further use, the glycol components separated from the terephthalate components and the terephthalate components purified.

The spray tower, crystallizer slurry tank and filter are designed and operated to perform the function indicated above.

In those embodiments which use a rectifier, substantial portion of MHET is returned from the rectifier to the reactor.

Nevertheless, some MHET is transported with the DMT. The present invention provides a convenient process for converting it to DMT. In those embodiments which do not use a rectifier, all of the product MHET is converted to DMT.

The following examples illustrate the invention used with product from a pressurized batch methanolysis reactor and a low pressure methanolysis reactor. Unless otherwise indicate, all percentages and parts are by weight.

EXAMPLE 1
(Conversion of MHET to DMT)

1 Part methylhydroxyethyl terephthalate (98.5% pure) was dissolved in 3 parts methanol to produce a clear solution. To this solution was added 4 parts of a mixture of 1.5 parts sodium hydroxide in 100 parts methanol. Within 30 seconds a crystalline precipitate formed. The solution was held, without agitation, for 30 minutes and then the precipitate was removed by filtration. The precipitate was analyzed by liquid chromatography and found to be 99.6% dimethyl terephthalate.

EXAMPLE 2
(Pressurized Batch Methanolysis Reactor)

Scrap polyethylene terephthalate was depolymerized in an autoclave as follows:

| Reaction Mixture | |
|---|---|
| PET | 264 g. |
| Diethylene Glycol | 33 g. |
| Triethylene Glycol | 17 g. |
| Methanol | 210 g. |
| Zinc Acetate (catalyst) | 0.8 g. |
| Reaction Conditions | |
| Temperature | 200° C. |
| Time | 4 hr. |
| Reaction Product | |
| DMT | 67% |
| MHET | 18% |
| Oligomers | 15% |

To 1 part of the above reaction product was added 1.5 parts of the sodium hydroxide/methanol mixture used in Example 1. The resulting mixture was heated at 54° C. and atmospheric pressure for 45 minutes. The reaction mixture was cooled, the methanol was removed by evaporation, the ethylene glycol was removed by filtration and the remaining solid was analyzed by liquid chromatography. The solid was found to be:

| DMT | 84.0% |
|---|---|
| MHET | 0.5% |
| Oligomers | 15.5% |

EXAMPLE 3

Polyethylene terephthalate was depolymerized in a 19L. pilot continuous reactor like that shown in U.S. Pat. No. 5,051,528. This was accomplished by passing heated methanol vapor through a melt comprising polyethylene terephthalate oligomer at 265° C. The reaction products, DMT, MHET and EG, were stripped from the reactor by excess methanol vapor. The product stream was condensed in a direct contact spray condenser with methanol as the cooling stream. Free methanol was removed from the product slurry by evaporation. Liquid chromatography of the remaining product slurry showed that DMT and MHET were present in a ratio of 74.1 parts DMT to 25.9 parts MHET.

The reactor was operated for a second time in the same way as described above, except that the methanol used as the cooling stream in the direct contact spray condenser contained 0.012% sodium hydroxide. Liquid chromatography of the product slurry showed that DMT and MHET were present in a ratio of 99.93 parts DMT to 0.07 parts MHET.

The reactor was operated a third time in the same way as described above, except that the methanol used in the spray condenser contained 0.012% potassium hydroxide. Liquid chromatography of the product slurry showed that DMT and MHET were present in a ratio of 99.6 parts DMT to 0.4 parts MHET.

The above three examples above show that MHET, alone or as an impurity in DMT recovered from polyester via high pressure or low pressure methanolysis, can be converted to DMT by caustic methanolysis. In addition, Example 3 shows that caustic methanolysis is a viable alternative to rectification as a means for removing MHET from the product stream of low pressure methanolysis apparatus.

The invention has been described by reference to preferred embodiments, but it will be understood changes can be made to the apparatus and process steps specifically described herein within the spirit and scope of the invention.

What is claimed is:

1. A process for converting a first mixture of dimethyl terephthalate and methylhydroxyethyl terephthalate to predominantly dimethyl terephthalate comprising the steps of:
    a) contacting the first mixture with a second mixture comprising an alcohol and an alkali metal hydroxide at a temperature in the range of from 0° C. to the boiling point of the alcohol and a pressure in the range of 0 psig to 30 psig, and
    b) allowing the reaction mixture formed in step a) to stand for a period of from 0.5 to 30 minutes.

2. A process of claim 1, wherein from 0.5 to 2 part by weight of the second mixture are contacted with 1 part of mixture.

3. A process of claim 1, wherein the second mixture comprises from 1 to 10 parts by weight alkali metal hydroxide per 100 parts alcohol.

4. A process of claim 1, wherein the alcohol is methanol.

5. A process of claim 1, wherein the alkali metal hydroxide is sodium hydroxide.

6. A process for converting a mixture of dimethyl terephthalate and methylhydroxyethyl terephthalate to predominantly dimethyl terephthalate comprising the steps of:
    a) forming a mixture of dimethyl terephthalate and methylhydroxyethyl terephthalate using apparatus that comprises:
        a dissolver for receiving polyester, and
        a reactor for depolymerizing polyester into monomer components,
    by
        i) adding polyester to the dissolver and combining it with melt from the reactor to reduce the chain length of the polyester,
        ii) transferring reduced chain length polyester from the dissolver to the reactor, iii) passing super-heated methanol through the reactor to depolymerize polyester into its constituent monomers,
iv) recovering monomer components from the output of the reactor; and
b) applying the process of claim 1 to the recovered ester components.

7. A process of claim 6, wherein the first mixture is formed using low pressure methanolysis apparatus and the second mixture is contacted with the first mixture in a spray tower in which it also serves to help crystallize dimethyl terephthalate.

* * * * *